US006989680B2

(12) United States Patent
Sosnowski et al.

(10) Patent No.: US 6,989,680 B2
(45) Date of Patent: *Jan. 24, 2006

(54) DETECTION OF COOLANT CONTAMINATION IN LUBRICATING FLUIDS

(75) Inventors: David R. Sosnowski, Lake Orion, MI (US); Richard W. Hirthe, Milwaukee, WI (US)

(73) Assignee: Eaton Corporation, Cleveland, OH (US)

(*) Notice: Subject to any disclaimer, the term of this patent is extended or adjusted under 35 U.S.C. 154(b) by 19 days.

This patent is subject to a terminal disclaimer.

(21) Appl. No.: 10/786,815

(22) Filed: Feb. 24, 2004

(65) Prior Publication Data

US 2005/0184733 A1    Aug. 25, 2005

(51) Int. Cl.
G01R 27/22 (2006.01)
G01R 27/26 (2006.01)
G01R 23/16 (2006.01)

(52) U.S. Cl. .................... 324/698; 324/683; 324/76.22
(58) Field of Classification Search ................ 324/698, 324/663, 444, 441, 76.77, 76.12, 76.13, 76.22, 324/553, 683, 667, 668
See application file for complete search history.

(56) References Cited

U.S. PATENT DOCUMENTS

| 4,743,855 | A  | 5/1988  | Randin |
| 6,278,281 | B1 | 8/2001  | Bauer et al. ................ 324/441 |
| 6,377,052 | B1 | 4/2002  | McGinnis et al. .......... 324/446 |
| 6,459,995 | B1 | 10/2002 | Collister |
| 6,511,851 | B1 | 1/2003  | Payne |
| 6,844,745 | B1* | 1/2005 | Schachameyer et al. ..... 324/698 |
| 6,861,851 | B2* | 3/2005 | Lvovich et al. ............. 324/698 |
| 2004/0085080 | A1* | 5/2004 | Schilowitz et al. ......... 324/698 |
| 2004/0239344 | A1* | 12/2004 | Hu ............................ 324/698 |
| 2005/0017738 | A1* | 1/2005 | Lin et al. .................... 324/698 |

OTHER PUBLICATIONS

U.S. Appl. No. 10/786,818, filed Feb. 24, 2004, Sosnowski et al.*
PCT Search report dated Jun. 22, 2005, Application No. PCT/IB2005/000421.
Lvovich V et al: "Characterization of Organic Surfactants ... " ASTM Special Technical Pub., American Soc. for Testing Materials, vol. 1402, 2001, pp., 157-173, ISSN:0066-0558.

* cited by examiner

Primary Examiner—Anjan Deb
(74) Attorney, Agent, or Firm—Anna M. Shih

(57) ABSTRACT

An impedance spectroscopy technique and system for detecting in real time engine coolant contamination in lubricant. A probe is disposed in the lubricant and the probe excited with an a.c. voltage frequency sweep over a selected frequency range. The current and current phase angle are measured at selected frequency intervals and the reactance and resistance computed and plotted at each frequency internal as Nyquist plots. The Nyquist minimum is determined at various lubricant temperatures and a database compiled. The probe is then excited in-situ and current measurements taken for a selected frequency lower than the Nyquist minimum to insure measurement of electrode surfaces characteristics. The reactance and resistance are then computed and the angle Θ of change (slope) of reactance with respect to resistance computed. The value of Θ is then compared with values of contamination concentration Ψ versus Θ in a database, and the value of Ψ determined by interpolation.

9 Claims, 3 Drawing Sheets

DETECTION OF COOLANT CONTAMINATION IN LUBRICATING FLUIDS

BACKGROUND OF THE INVENTION

The present invention relates to the employment of impedance spectroscopy to determine the chemical condition of lubricating fluids as, for example the condition of lubricants used in an internal combustion engine.

A known technique for monitoring in real time the condition of engine lubricant is described in U.S. Pat. No. 6,278,281 assigned to the assignee of the present invention and which describes using the differential of current measurements or impedance for separate current measurements taken at high and low frequencies indicative respectively of bulk fluid and electrode surface impedance. Such differential impedance spectroscopy has proven to be a useful technique for enabling a transducer to provide a continuous signal indicative of the engine lubricant during operation of the engine.

However, it has been found that there is also the need to readily identify the presence of any engine coolant leaking from the engine coolant system into the engine lubricant.

Although the aforesaid known technique of differential impedance spectroscopy has been found useful for monitoring changes in engine lubricant due to the effect of products of combustion, it has not be found limited to tracking such effects.

The aforesaid technique is described in U.S. Pat. No. 6,278,281 although useful, has not been found satisfactory for detecting the presence of coolant in the engine lubricant and it has been found quite difficult to rationalize the behavior of the fluid over a range of temperatures where the amount of coolant contamination is varying due to progressive leakage into the engine lubricant. Thus, it has been desired to provide a simple, low cost and easy to install way or means of correlating the changes in the engine lubricant due to engine coolant contamination and in order to provide an accurate real time indication of the amount of coolant contamination in the engine lubricant.

BRIEF SUMMARY OF THE INVENTION

The present invention provides for measuring the presence of engine coolant contamination in lubricant, particularly coolant of the type comprising a mixture of ethylene or propylene glycol in water. The invention employs impedance spectroscopy with sensing probe excitation by a relatively low voltage alternating current measured at intervals during a frequency sweep which includes frequencies indicative of bulk fluid properties and surface electrode properties with reference to the impedance calculated from the current measurements. The reactive impedance is plotted as a function of the resistance for current measurements taken at selected intervals over the frequency sweep (Nyquist plot); and, the minimum reactance is determined from the plot (Nyquist minimum). The frequency $f_{NM}$ associated with the Nyquist minimum is determined from the current measurements. A database is developed for the Nyquist minima frequencies $f_{NM}$ of the uncontaminated lubricant at various temperatures, over a range of temperatures for which the lubricant is in service, for known values of coolant contamination. An impedance probe is then excited in situ during engine operation with a frequency sweep; and, the Nyquist minimum is determined. The impedance is computed for frequencies less than the frequency corresponding to the Nyquist minimum to ensure current measurements indicative of the electrode surface properties. The angle $\Theta$ of the slope of the change of reactance with respect to resistance is then computed; and, the value of $\Theta$ compared with a database of values $\Theta$ for known concentrations of coolant contamination $\Psi$; and, the value of $\Psi$ then determined by interpolation.

DETAILED DESCRIPTION OF THE INVENTION

Figure 1:
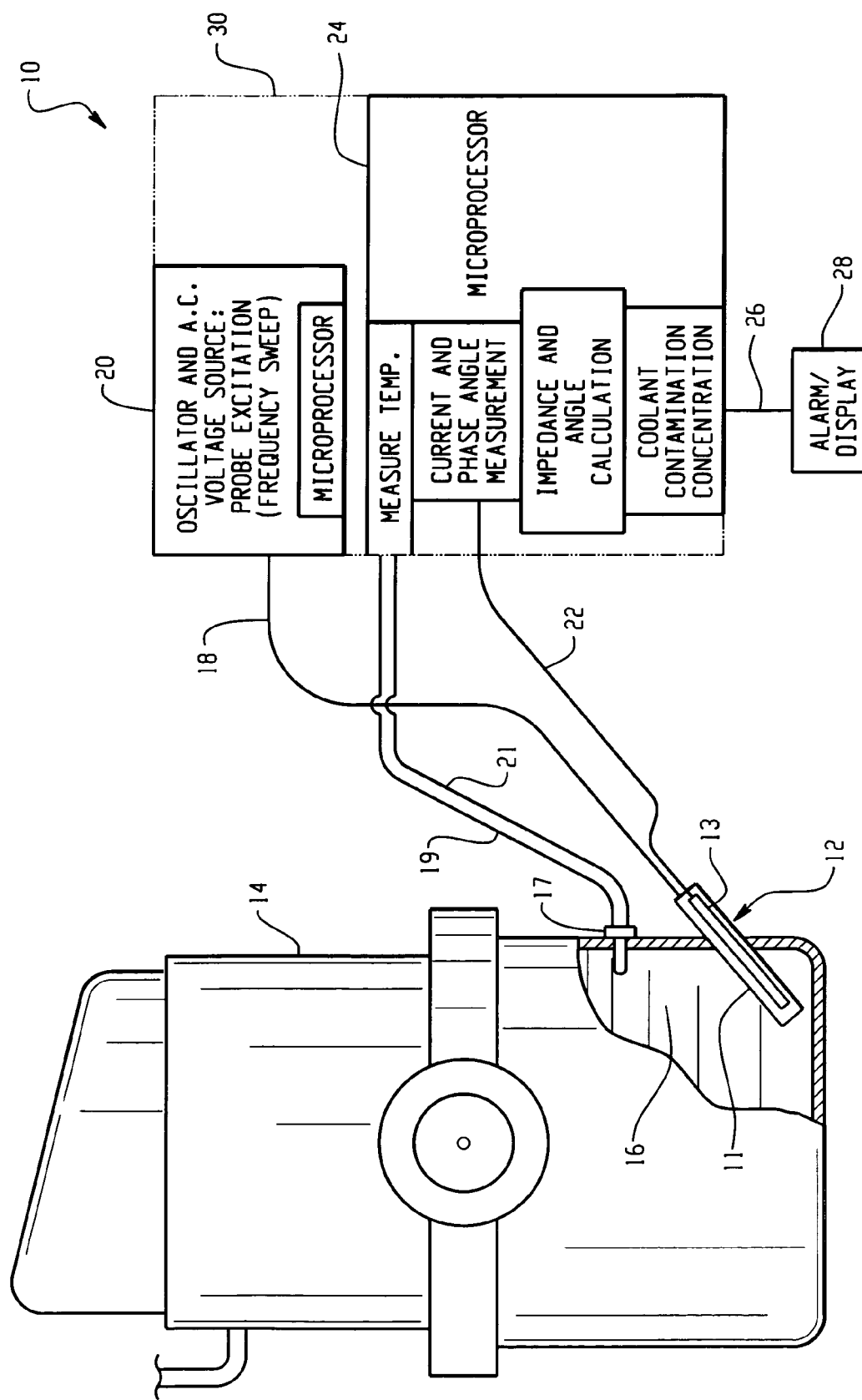
FIG. 1 is a pictorial representation of an impedance probe system for providing an electrical indication of coolant contamination of lubricant.

Referring to FIG. 1, the invention is indicated generally at 10 and includes a probe 12 having a pair of spaced electrodes 11, 13, which probe is inserted into the crankcase of an engine 14 and immersed in the engine lubricant indicated at 16. The probe 12 has connections for its electrodes extending externally of the engine. The probe 12 has a first electrode 11 connected to a controller 30 along line 18; and, a second probe electrode 13 is connected along line 22 to the controller. Controller 30 includes a source of low voltage alternating current indicated at 20; and, in the presently preferred practice of the invention controller 30 generates an excitation voltage in the range of about 0.01 Hz to 10 kHz. A voltage source 20 is connected along line 18 to the probe electrode 11.

Controller 30 also includes a microprocessor 24 and performs measurement of the current magnitude and the current phase angle and performs the impedance angle calculations as will be hereinafter described to determine the amount of contamination of the lubricant 16. The controller 30 may also output a signal along line 26 to an alarm/display 28 for providing an indication of prohibitive contamination of the engine lubricant.

Figure 2:
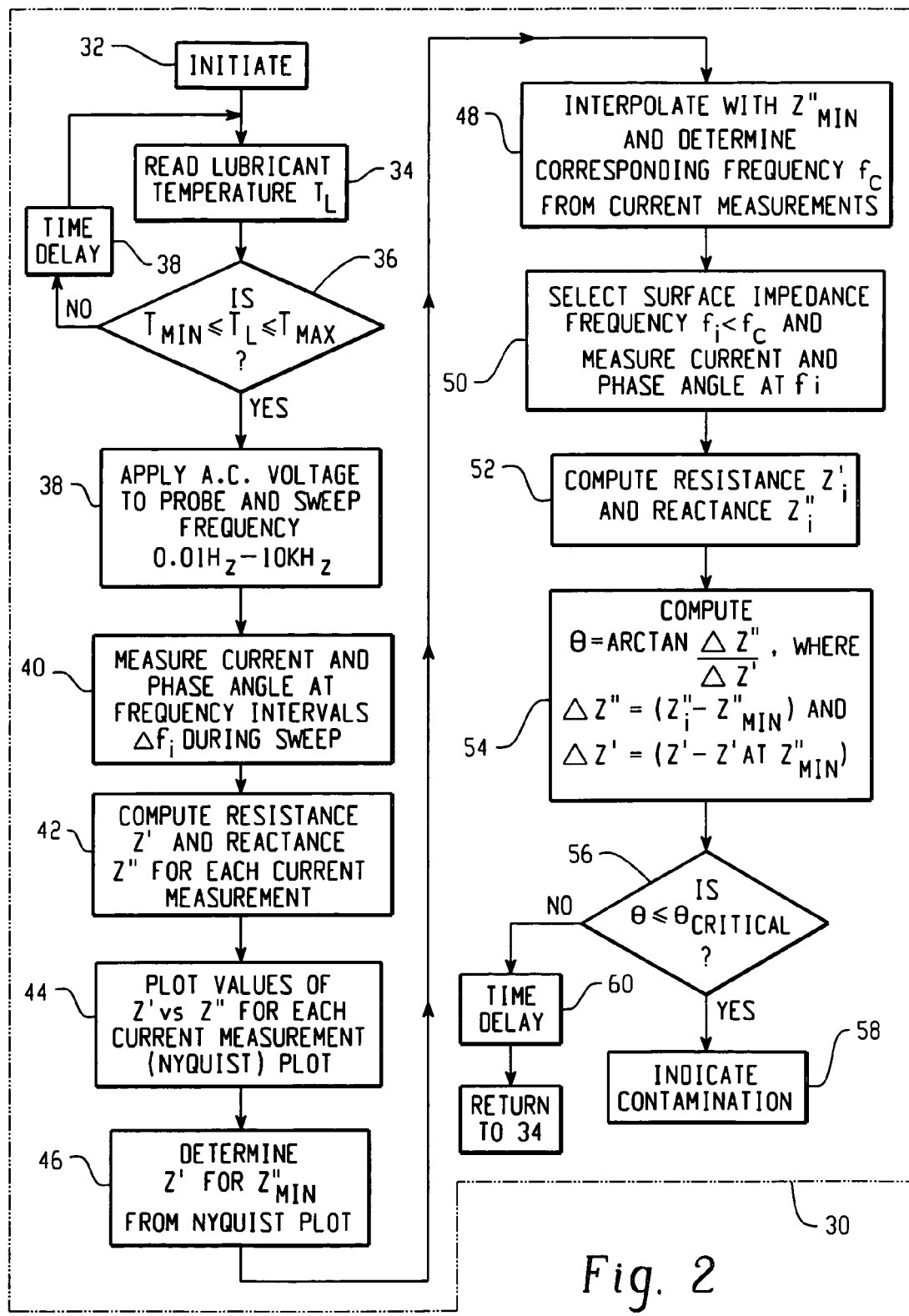
FIG. 2 is a block diagram of the operation of the system of FIG. 1.

Referring to FIG. 2, the operation of the controller 30 is indicated in block diagram wherein the system is initiated at step 32 and proceeds to read the lubricant temperature $T_L$ at step 34 and proceeds to step 36 to make the determination whether $T_L$ is within the desired limits $T_{MIN}$ and $T_{MAX}$ which are predetermined. In the present practice of the invention it has been found satisfactory to set $T_{MIN}$ at 100° C. and $T_{MAX}$ at 120° C. for normal engine operation. If the determination in step 36 is negative, the system proceeds to a time delay 38 and then returns to step 34.

If the determination in step 36 is affirmative, the system proceeds to step 38 and applies an AC voltage to the probe 12 and sweeps the frequency over a desired range, which is preferably in the range of about 0.01 Hz to 10 kHz. The system then proceeds to step 40 wherein the current and phase angle are measured at desired frequency intervals. It has been found satisfactory during the sweep to set the frequency interval $\Delta f_i$ at about one-tenth of each decade or order of magnitude of frequency sweep.

The system then proceeds to step 42 and calculates the resistance Z' and reactance Z" for each current measurement taken in step 40.

The system then plots the values of Z' as a function of Z" for each current measurement taken in step 40 and produces at step 44 a Nyquist plot of the frequency sweep. From the Nyquist plot of step 44, the system proceeds to step 46 and determines the minimum reactance $Z''_{MIN}$ from the Nyquist plot and the corresponding resistance $Z'$ at the Nyquist minimum.

The system then proceeds to step 48 and determines the frequency $f_c$ corresponding to the Nyquist minimum $Z''_{MIN}$ from the current measurement data by interpolation from the data and calculations of steps 40 and 42.

The system then proceeds to step 50 and selects a frequency $f_i$ less than the frequency $f_c$ determined in step 48. The system then proceeds to compute the resistance $Z'_i$ and reactance $Z''_i$ at step 52.

At step 54 the controller computes the angle $\Theta$ or rate of change of $Z''$ with respect to $Z'$ for the values computed in step 52 with reference to $Z''_{MIN}$ and $Z'_{@Z''MIN}$. As set forth in step 52, $$\Theta = \arctan\frac{\Delta Z''}{\Delta Z'},$$

where $\Delta Z''$ equals $(Z''_i - Z''_{min})$; and, $\Delta Z'$ equals $(Z'_i - Z'_{@Z''min})$.

The system then proceeds to step 56 and makes a determination whether $\Theta$ is equal to a less than $\Theta_{critical}$. In the present practice of the invention, for diesel engine lubricant, it has been found satisfactory to employ a value of about 40° for $\Theta_{critical}$. However, if $\Theta$ is substantially less than $\Theta_{@Z''MIN}$, then the lubricant is considered coolant contaminated.

Figure 3:
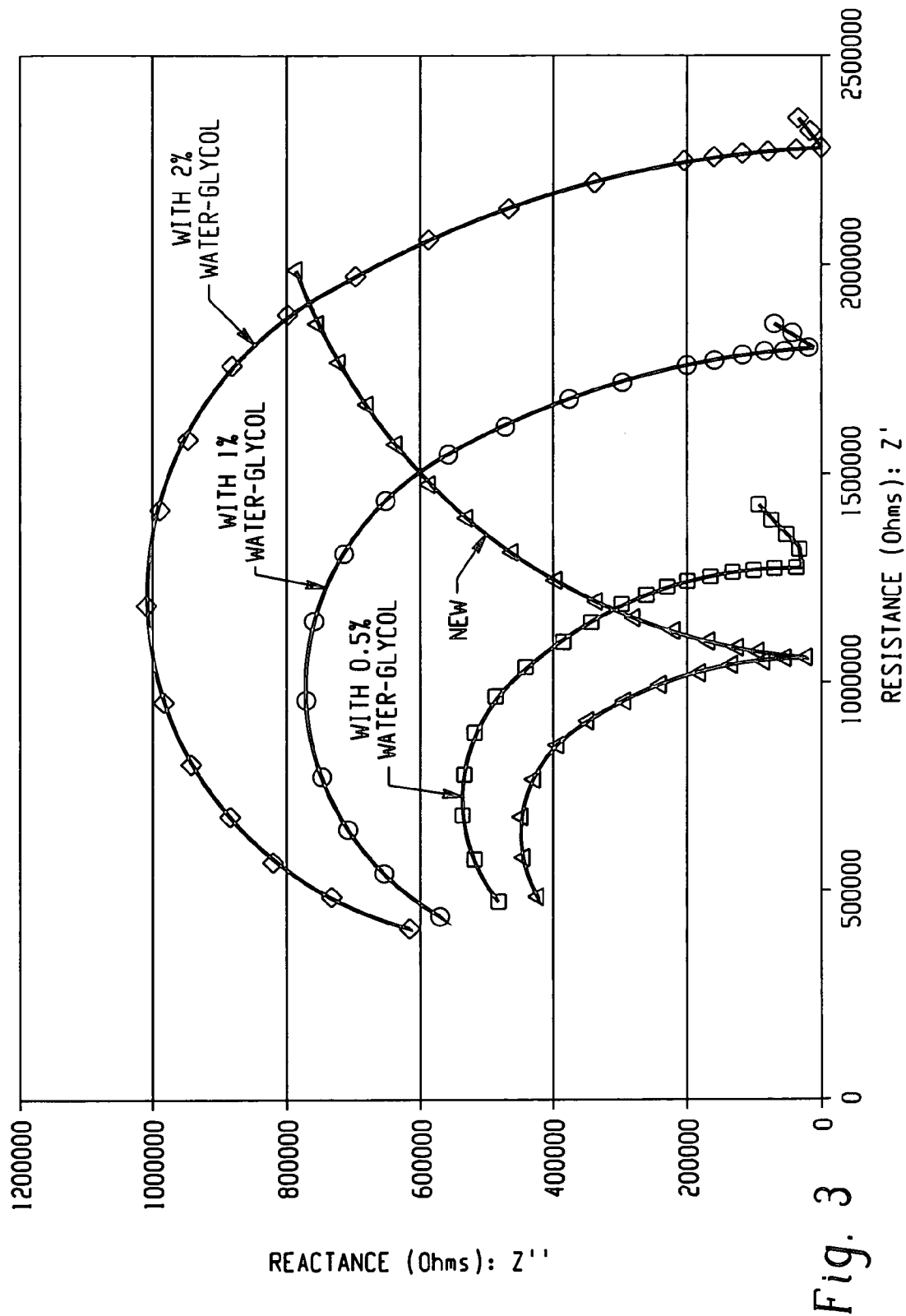
FIG. 3 is a Nyquist plot for different levels of coolant contamination of diesel engine lubricant.

If the determination in step 56 is positive, system wise a signal to indicate contamination at step 58. However, if the determination at step 56 is negative, the system then proceeds to a time delay 58 and then returns to step 34. Referring to FIG. 3, Nyquist plots are illustrated for new and contaminated SAE CI-4, 15W40 engine lubricant contaminated with three different concentration levels of a 50/50 mixture of ethylene glycol and water. It will be noted from FIG. 3 that the rate of change of $Z''$ with respect to $Z'$ to the right hand side of a Nyquist minima is much less as the level of contamination increases. Furthermore, it will be noted a pronounced increase in the value of resistance at which the Nyquist minimum occurs for increasing coolant contamination.

The present invention thus provides a relatively high degree of resolution of the change in reactance with respect to resistance from excitation of a probe disposed in the engine lubricant based upon current measurements taken on the lower frequency side of the Nyquist minimum for a given frequency sweep of the excitation voltage. The present invention thus provides a simple yet effective way of providing in situ real time indication of coolant contamination in engine lubricant during operation.

Although the invention has hereinabove been described with respect to the illustrated embodiments, it will be understood that the invention is capable of modification and variation and is limited only by the following claims.

What is claimed is:

1. A method of monitoring the presence of engine coolant contamination in lubricant comprising:
   (a) disposing at least two electrodes in the lubricant and applying a relatively low voltage alternating current to one of said electrodes and sweeping the frequency of the voltage over a predetermined range;
   (b) measuring the current and phase angle at a second of said electrodes at predetermined frequency intervals during the sweep and computing the reactance and resistance at each current measurement;
   (c) determining the least value of reactance $Z''_{min}$ from said computing;
   (d) selecting a frequency $f_i$, less than the frequency corresponding to $Z''_{min}$;
   (e) exciting said one electrode with said voltage at the frequency $f_i$ and measuring the current and phase angle at said second electrode and computing the reactance $Z''_i$ and the resistance $Z'_i$;
   (f) determining the parameter $$\Theta = \arctan\frac{\Delta Z''}{\Delta Z'},$$

where $\Delta Z''$ is the change in reactance $(Z''_i - Z''_{min})$ and $\Delta Z'$ is the change in resistance $(Z'_i - Z'_{@Z''min})$; and,
   (g) providing an indication that coolant contamination exists when $\Theta$ reaches a predetermined value.

2. The method defined in claim 1, wherein said step of measuring current includes measuring current over the sweep at frequencies indicative of bulk fluid impedance and at frequencies indicative of surface electrode impedance.

3. The method defined in claim 1, wherein said step of providing an indication that contamination exists includes providing such an indication when $\Theta$ reaches an angle of about 40°.

4. The method defined in claim 1, wherein said step of disposing at least two electrodes includes arranging the electrodes in spaced concentric arrangement.

5. The method defined in claim 4, wherein said step of applying a relatively low voltage alternating current includes measuring the lubricant temperature and delaying the said applying until the temperature is within predetermined limits.

6. The method defined in claim 1, wherein said step of sweeping the frequency includes sweeping in the range of about 0.01 Hz to 10 kHz.

7. The method defined in claim 1, wherein said step of applying a relatively low voltage includes applying an a.c. voltage in the range of about 0.10 to 2.0 volts.

8. The method defined in claim 1, wherein said step of measuring current at predetermined intervals includes measuring the current at intervals of about one-tenth of each decade of frequency sweep.

9. The method defined in claim 1, wherein said step of providing an indication that contamination exists includes providing such when $\Theta$ is about 45° less than the value of $\Theta$ for new uncontaminated lubricant.

* * * * *